United States Patent
Franer

(10) Patent No.: US 9,814,491 B2
(45) Date of Patent: *Nov. 14, 2017

(54) PLEATED TROCAR SEAL

(71) Applicant: Ethicon Endo-Surgery, LLC, Guaynabo, PR (US)

(72) Inventor: Paul T. Franer, Cincinnati, OH (US)

(73) Assignee: ETHICON LLC, Guaynabo, PR (US)

( * ) Notice: Subject to any disclaimer, the term of this patent is extended or adjusted under 35 U.S.C. 154(b) by 503 days.

This patent is subject to a terminal disclaimer.

(21) Appl. No.: 14/255,592

(22) Filed: Apr. 17, 2014

(65) Prior Publication Data

US 2014/0316338 A1    Oct. 23, 2014

Related U.S. Application Data

(63) Continuation of application No. 12/829,727, filed on Jul. 2, 2010, now Pat. No. 8,728,037, which is a continuation of application No. 11/379,168, filed on Apr. 18, 2006, now Pat. No. 7,789,861.

(51) Int. Cl.
*A61M 5/178* (2006.01)
*A61B 17/34* (2006.01)
*B65B 55/12* (2006.01)

(52) U.S. Cl.
CPC ...... *A61B 17/3498* (2013.01); *A61B 17/3462* (2013.01); *A61B 17/3478* (2013.01); *B65B 55/12* (2013.01); *A61B 2017/3464* (2013.01)

(58) Field of Classification Search
CPC ............ A61B 17/3462; A61B 17/3498; A61B 17/3478; A61B 2017/3464
USPC ....................................... 604/167.03, 167.01
See application file for complete search history.

(56) References Cited

U.S. PATENT DOCUMENTS

| | | | |
|---|---|---|---|
| 3,839,841 A | * | 10/1974 | Amplatz .......... A61M 25/0009 264/320 |
| 4,112,932 A | | 9/1978 | Chiulli |
| 4,535,773 A | | 8/1985 | Yoon |
| 4,601,710 A | | 7/1986 | Moll |
| 4,654,030 A | | 3/1987 | Moll et al. |
| 4,902,280 A | | 2/1990 | Lander |
| 4,929,235 A | | 5/1990 | Merry et al. |
| 4,931,042 A | | 6/1990 | Holmes et al. |
| 5,030,206 A | | 7/1991 | Lander |
| 5,104,382 A | | 4/1992 | Brinkerhoff et al. |
| 5,114,407 A | | 5/1992 | Burbank |
| 5,197,955 A | | 3/1993 | Stephens et al. |

(Continued)

FOREIGN PATENT DOCUMENTS

RU    2159085 C1    11/2000

OTHER PUBLICATIONS

International Search Report, International Application No. PCT/US2007/066759, Sep. 26, 2007.

(Continued)

*Primary Examiner* — Kevin C Sirmons
*Assistant Examiner* — Tiffany Legette-Thompson

(57) ABSTRACT

A trocar seal comprising an elastomeric membrane having an opening adapted to receive a surgical instrument. The membrane is configured with a plurality of pleats circumscribing the opening and extending laterally from opening. The pleats comprise a plurality of pleat walls increasing in height as the pleats extend laterally from the opening. In one embodiment, the pleats are conically arranged.

16 Claims, 5 Drawing Sheets

(56) References Cited

U.S. PATENT DOCUMENTS

| | | |
|---|---|---|
| 5,209,737 A | 5/1993 | Ritchart et al. |
| 5,256,147 A | 10/1993 | Vidal et al. |
| 5,275,583 A | 1/1994 | Crainich |
| 5,308,336 A | 5/1994 | Hart et al. |
| 5,312,354 A | 5/1994 | Allen et al. |
| 5,342,315 A | 8/1994 | Rowe et al. |
| 5,350,364 A | 9/1994 | Stephens et al. |
| 5,350,393 A | 9/1994 | Yoon |
| 5,385,553 A | 1/1995 | Hart et al. |
| 5,391,153 A | 2/1995 | Haber et al. |
| 5,405,328 A | 4/1995 | Vidal et al. |
| 5,407,433 A | 4/1995 | Loomas |
| 5,411,515 A | 5/1995 | Haber et al. |
| 5,431,635 A | 7/1995 | Yoon |
| 5,443,452 A | 8/1995 | Hart et al. |
| 5,512,053 A | 4/1996 | Pearson et al. |
| 5,535,809 A | 7/1996 | White |
| 5,545,142 A | 8/1996 | Stephens et al. |
| 5,549,564 A | 8/1996 | Yoon |
| 5,551,947 A | 9/1996 | Kaali |
| 5,554,137 A | 9/1996 | Young et al. |
| 5,554,167 A | 9/1996 | Young et al. |
| 5,569,289 A | 10/1996 | Yoon |
| 5,584,850 A | 12/1996 | Hart et al. |
| 5,591,190 A | 1/1997 | Yoon |
| 5,607,440 A | 3/1997 | Danks et al. |
| 5,609,604 A | 3/1997 | Schwemberger et al. |
| 5,628,732 A | 5/1997 | Antoon, Jr. et al. |
| 5,645,076 A | 7/1997 | Yoon |
| 5,645,556 A | 7/1997 | Yoon |
| 5,669,885 A | 9/1997 | Smith |
| 5,674,184 A | 10/1997 | Hassler, Jr. |
| 5,674,237 A | 10/1997 | Ott |
| 5,685,820 A | 11/1997 | Riek et al. |
| 5,697,947 A | 12/1997 | Wolf et al. |
| 5,720,761 A | 2/1998 | Kaali |
| 5,752,938 A | 5/1998 | Flatland et al. |
| 5,792,113 A | 8/1998 | Kramer et al. |
| 5,797,944 A | 8/1998 | Nobles et al. |
| 5,810,863 A | 9/1998 | Wolf et al. |
| 5,827,228 A * | 10/1998 | Rowe ............... A61B 17/3417 604/167.02 |
| 5,989,224 A | 11/1999 | Exline et al. |
| 6,551,282 B1 | 4/2003 | Exline et al. |
| 6,767,340 B2 | 7/2004 | Willis et al. |
| 7,481,795 B2 | 1/2009 | Thompson et al. |
| 7,789,861 B2 * | 9/2010 | Franer ............... A61B 17/3462 604/167.01 |
| 8,147,457 B2 | 4/2012 | Michael et al. |
| 8,728,037 B2 | 5/2014 | Franer |
| 2004/0260244 A1 | 12/2004 | Piechowicz et al. |
| 2005/0203467 A1* | 9/2005 | O'Heeron ......... A61B 17/3498 604/249 |
| 2005/0288634 A1 | 12/2005 | O'Heeron et al. |
| 2006/0220325 A1 | 10/2006 | McFarlane |

OTHER PUBLICATIONS

International Preliminary Report, International Application No. PCT/US2007/066759, dated Oct. 30, 2008.

* cited by examiner

PLEATED TROCAR SEAL

BACKGROUND

The present invention relates general to endoscopic surgical procedures, and in particular, to trocars used in such procedures.

The use of endoscopic procedures in surgery has become widely accepted. The term "endoscopic" refers to all types of minimally invasive surgical procedures including laparoscopic and arthroscopic procedures. Endoscopic surgery has numerous advantages compared to traditional open surgical procedures, including reduced trauma, faster recovery, reduced risk of infection, and reduced scarring.

Numerous endoscopic instruments have been developed that allow the surgeon to perform complex surgical procedures with minimal incisions into the skin and tissue surrounding a particular body cavity or anatomical region. In order to introduce the endoscopic instrumentation into the body cavity, a device known as a "trocar" is often used to puncture and/or cannulate the wall of the body cavity. Trocars are widely known in the art and typically comprise an obtruator and a cannula. The obtruator typically includes a sharply pointed or appropriately structured tip that facilitates penetration of the body cavity wall. The cannula provides a channel or opening through the body cavity wall through which endoscopic instruments may be introduced and removed by the surgeon.

Endoscopic surgery is often performed with an insufflatory fluid present within the body cavity, such as carbon dioxide or saline, to provide adequate space to perform the intended surgical procedures. The insufflated cavity is generally under pressure and is sometimes referred to as being in a state of pneumoperitoneum. It is common for a sealing arrangement or seal assembly to be used in association with the trocar to maintain pneumoperitoneum. The seals will generally prevent the insufflatory fluid from escaping while an endoscopic instrument is positioned in the trocar cannula.

No one has previously made or used a trocar or seal in accordance with the present invention.

BRIEF DESCRIPTION OF DRAWINGS

While the specification concludes with claims which particularly point out and distinctly claim the invention, it is believed the invention will be better understood from the Wowing description taken in conjunction with the accompanying drawings illustrating some non-limiting examples of the invention. Unless otherwise indicated, the figures are drawn to scale and like reference numerals identify the same elements.

DETAILED DESCRIPTION

Figure 1:
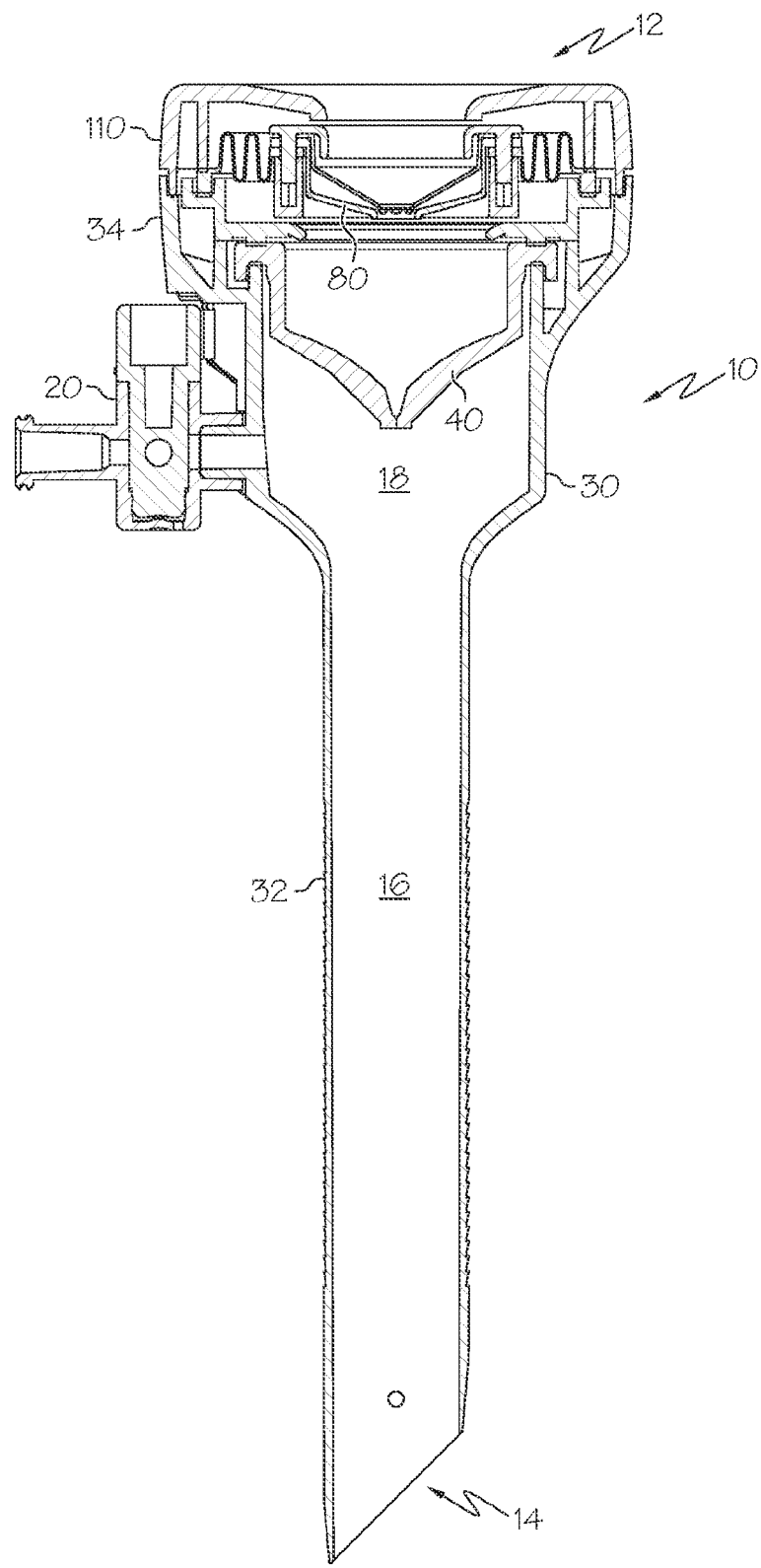
FIG. 1 depicts a cross-sectional view of a trocar.

FIG. 1 depicts a cross-sectional view of a trocar (10). During typical use the distal end (14) will be inserted through the body wall into the cavity, and the proximal end (12) will be positioned outside the patient. A cannula (16) opens through the distal end (14) and is in fluid communication with a seal housing (18). The size of the cannula (16) can vary widely, but in the present example the inside diameter is about 12.9 mm. A valve (20), shown here as a stopcock, permits the surgeon to selectively introduce or relieve pressurized insufflation fluid through the trocar (10) to the body cavity. Optionally, the trocar (10) may include obtruator (not shown).

The seal housing (18) contains a seal arrangement comprising a closure valve (40) and an instrument seal (80) that work together to maintain pneumoperitoneum. In this example, the closure valve (40) is a single-silted "duck bill" valve; however, other types of closure valves may also be used, including flapper valves, multi-silted duck bill valves, and the like. When an endoscopic instrument is passed though the proximal end (12) through the closure valve (40), the valve will open but will generally not provide a complete seal against the instrument. When the instrument is removed from the trocar (10), the closure valve (40) closes and substantially prevents insufflation fluid from escaping through the trocar (10). The instrument seal (80) seals against the instrument to prevent insufflation fluid from escaping through the trocar (10); however, the instrument seal (80) generally will not maintain pneumoperitoneum unless an instrument is positioned in the trocar (10). In this example, the instrument seal (80) "floats" within the valve housing (8) such that the seal (80) can move laterally relative the trocar (10) centerline.

Figure 2:
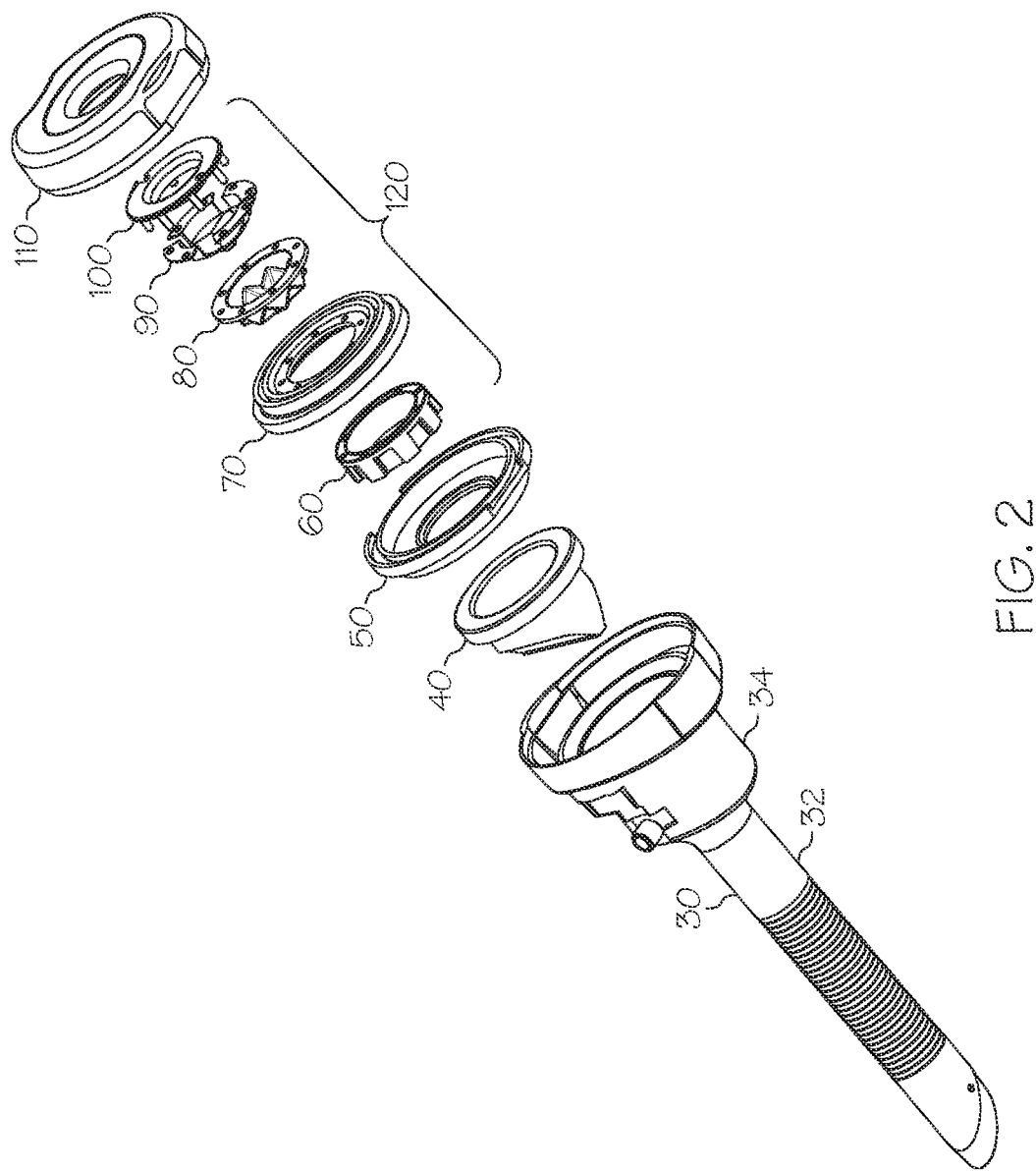
FIG. 2 depicts an exploded view of the trocar of FIG. 1.

FIG. 2 depicts an exploded view of the trocar (10) and helps illustrate the assembly of the component parts. The lower body (30) includes an elongate tube portion (32), which defines the cannula (16), and a housing portion (34). The upper body (110) attaches to the housing portion (34), which together provide a housing wall to define the seal housing (18). The closure valve (40) is positioned and seated in the housing portion (34). The retainer ring (50) is positioned and seated against the closure valve (40) and sandwiches a flange on the closure valve (40) against the housing portion (34) to provide a seal at that location. These components can be made from a variety of different materials. For instance, in the present example the lower body (30), retainer ring (50), and upper housing (110) are formed from relatively rigid plastic such as polycarbonate, and the closure valve (40) is formed from a relatively soft elastomer such as polyisoprene; however, other materials could also be used.

The instrument seal assembly (120) is sandwiched between the retainer ring (50) and the upper body (110) to provide a seal at that location. The instrument seal assembly (120) includes an anchor (60), bellows (70), instrument seal (80), protectors (90), and retainer (100). The posts on the retainer (100) align with the corresponding holes on the other components of the assembly (120). The bellows (70), instrument seal (80), and protectors (90) are sandwiched between the retainer (100) and the anchor (60). An interference fit between the retainer (100) posts and anchor (60) holes keep the assembly (120) in compression. The protectors (90) comprise four sequentially overlapping plates to protect the instrument seal (80) from perforating or tearing due to surgical instruments. The components of the instrument seal assembly (120) can be made from a variety of different materials with a range of different material properties. For instance, in the present example the anchor (60) and retainer (100) are formed from relatively rigid plastic such as polycarbonate, the bellows (70) and instrument seal (80) are formed from a relatively soft elastomer such as polyisoprene, and the protectors (90) are formed from a pliant but semi-rigid plastic such as pellathane; however, other materials could also be used.

Figure 3:
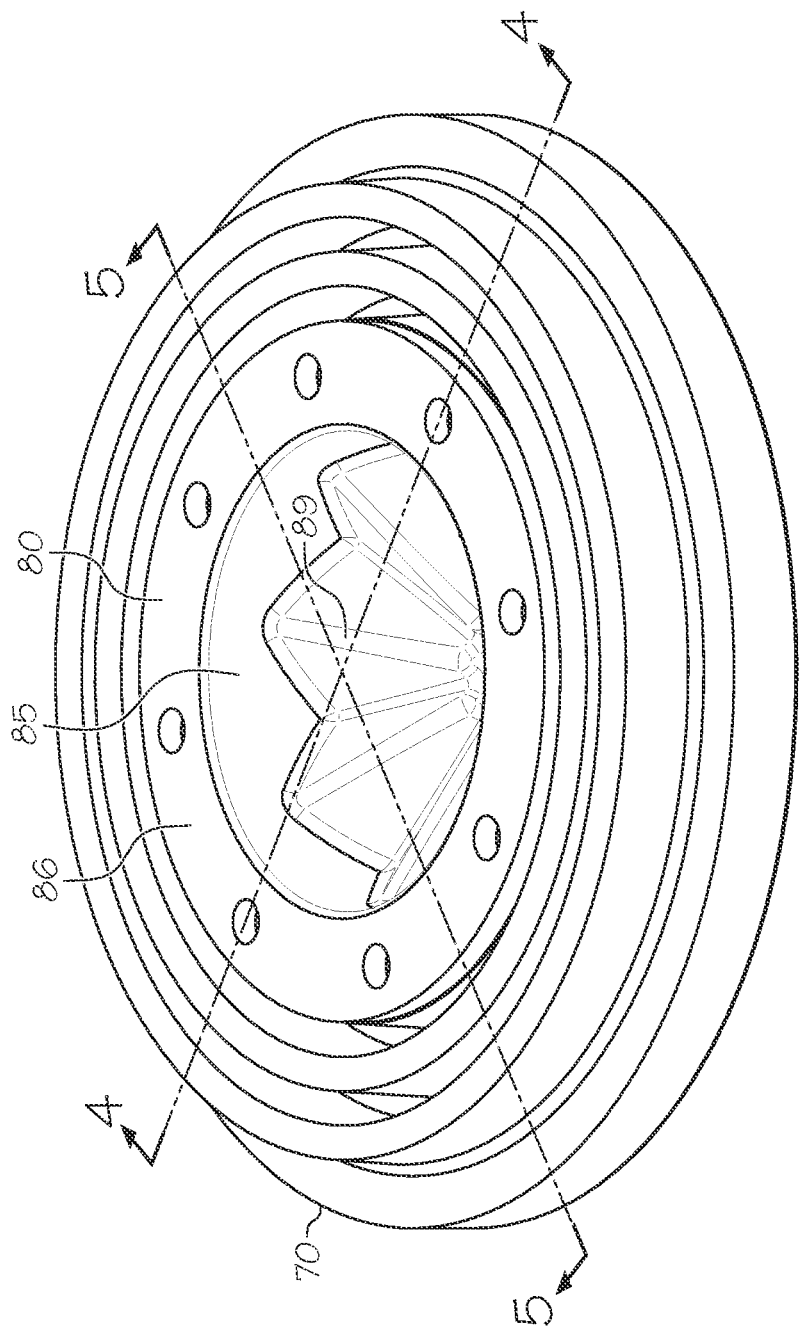
FIG. 3 depicts a perspective view of an instrument seal and bellows.
Figure 4:
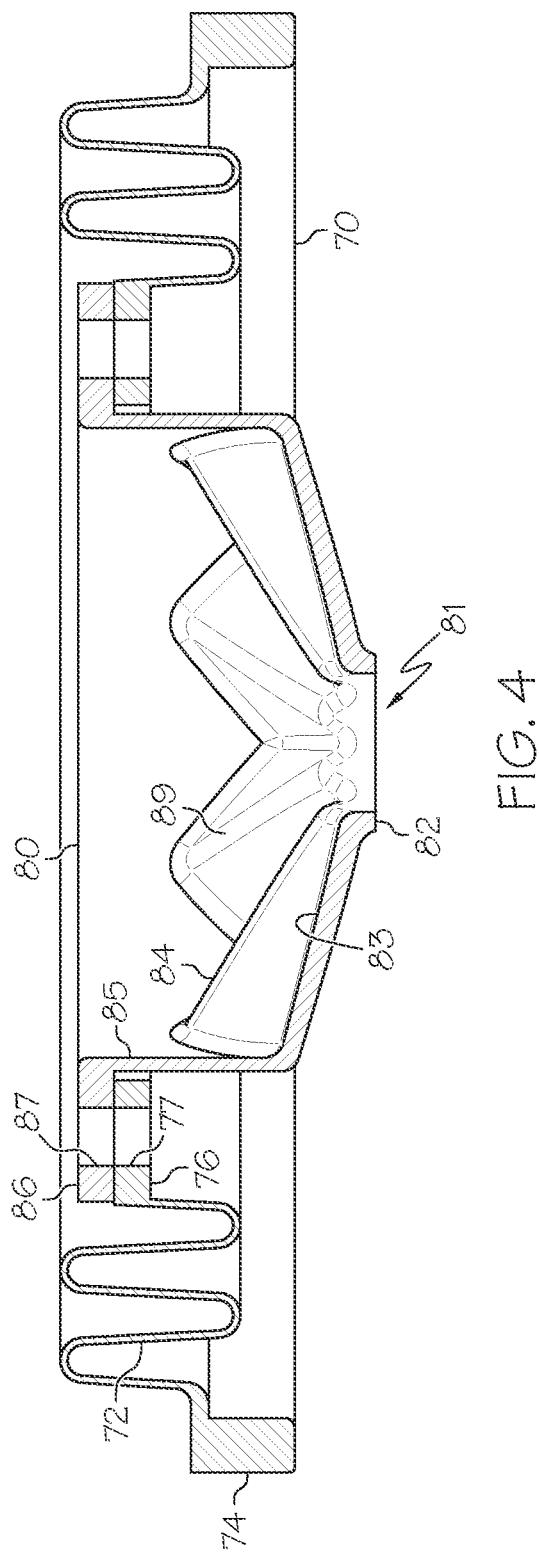
FIG. 4 depicts a cross-sectional view from FIG. 3.
Figure 5:
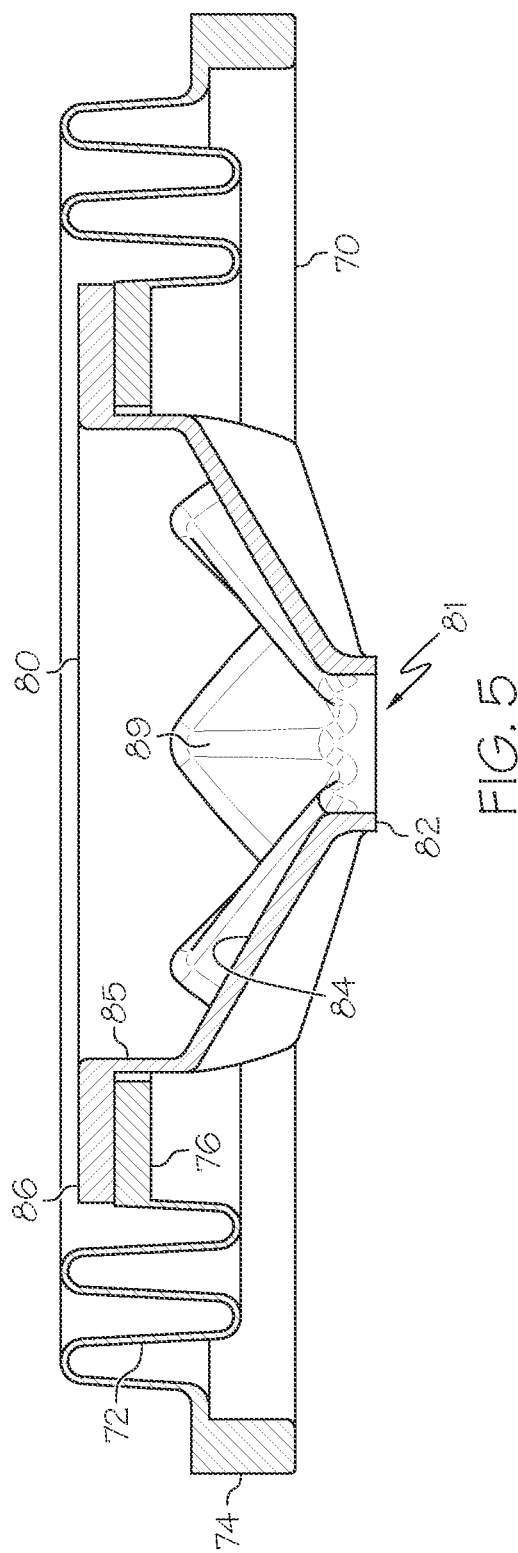
FIG. 5 depicts another cross-sectional view from FIG. 3.

FIGS. 3-5 illustrate the bellows (70) and instrument seal (80). The bellows (70) are an elastomeric membrane comprising a circular lateral flange (74), a circular medial flange (76), and circumferential pleats (72) positioned between the flanges (74, 76). The pleats (72) provide lateral pliancy so the assembly (120) can float. The medial flange (76) includes a plurality of holes (77) that align with the retainer (100) posts. The lateral flange engages the housing wall creating a seal at that location.

The instrument seal (80) is an elastomeric membrane having lips (82) defining an opening (81) adapted to receive and sealingly engage an endoscopic surgical instrument. The size of the opening (81) in its relaxed state may vary widely, but in the present example the inside diameter is between 3.8 and 4.0 mm. The instrument seal (80) of the present example is sufficiently elastic that the opening (81) can expand to sealingly engage instruments having diameters of up to 12.9 mm. A plurality of pleats (89) circumscribe the opening (81) and extend laterally from opening (81). As shown in this example, the instrument seal (80) comprises eight linear, pleats (89); however, greater or fewer or non-linear pleats could also be used. In this embodiment, the pleats (89) are conically arranged. A wall section (85) circumscribes and is connected to the pleats (89). As shown here, the inside diameter of the wall section (85) is between 17.7 and 17.9 mm. A radial flange (86) extends laterally from the wall section (85) and includes a plurality of holes (87) that align with the retainer (100) posts.

Each pleat (89) comprises a pleat wall extending between the pleat peak (84) and pleat valley (83). The height of the pleat walls can be measured along the wall surface from the peak (84) to the valley (83). As shown here, the pleat walls each have a variably height that tapers medially. Accordingly, the pleat walls increase in height as the pleats extend laterally from the opening (81). Among other advantages, the pleats (89) help to reduce hoop stresses when an instrument is positioned in the opening (81), thus reducing friction between the instrument and the trocar (10). Reduced hoop stresses facilitate a thicker wall thickness to be used while providing similar or reduced drag forces than non-pleated lip seal designs, thus increasing seal durability.

Optionally, the geometry of the pleats (89) can be designed to minimize or eliminate hoop stress in the pleated portion of the seal (80) when an instrument is introduced. In one embodiment, this geometric relationship conforms to the following equation:

$$h \geq \frac{\pi}{P}\sqrt{r^2 + r_i^2 - r_{id}^2}$$

where:
h=pleat wall height as a function of radius
r=radius
$r_i$=radius of largest instrument designed for insertion through seal
$r_{id}$=radius at inside diameter of pleat section of seal
P=number of pleats A pleat design will substantially conform to the this equation if it complies with the essence of this equation, even if the pleat geometry varies insignificantly. For example, geometric variances to accommodate molding or other manufacturing considerations would substantially conform to this equation. As another example, a pleat design that satisfies the equation at all locations excepts for minor variances at the inside or outer diameters of the pleat section of the seal would nevertheless substantially conform to the equation.

As shown in the figures, the pleats (89) form a generally frustoconical shape bounded by the wall section (85) and the lip (82). In this example, the slope of the frustoconical shape is greater on the proximal side than the distal side, with both the proximal and distal surfaces sloping distally toward the opening (81). Alternatively, both surfaces could slope proximally. In another variation, the proximal surface could slope distally and the distal surface could slope proximally. In yet another variation, one of the surfaces could slope while the other could be planar. It is also contemplated that both the surfaces could have the same slope or both could be planar.

The lip (82) in this example has a cylindrical portion, which when intersected with the pleats (89) results in a crown-shaped surface with proximally pointing tips corresponding to each peak (84). Similarly, the wall section (85) in this example has a cylindrical portion, which when intersected with the pleats (89) results in an upside crown-shaped surface with distally pointing tips corresponding to each valley (83). Naturally, the lip (82) and/or wall section (85) could be non-cylindrical, such as having a straight or curved taper.

The lateral flange (74) is compressed between the retainer ring (50) and the upper body (10) to provide a seal against the housing wall. The medial flange (76) and radial flange (86) are compressed between the anchor (60) and the retainer (100) to provide a seal. When an instrument is positioned and sealed in the opening (81), pneumoperitoneum can be maintained. While the bellows (70) and instrument seal (80) are shown in this example as separate parts, it is contemplated that the bellows (70) and instrument seal (80) can be formed as a unitary part.

Preferably, the trocars will be processed before surgery. First, a new or used trocar is obtained and if necessary cleaned. The trocar can then be sterilized. In one sterilization technique, the trocar is placed in a closed and sealed container, such as a plastic or TYVEK bag. The container and trocar are then placed in a field of radiation that can penetrate the container, such as gamma radiation, x-rays, or high-energy electrons. The radiation kills bacteria on the trocar and in the container. The sterilized trocar can then be stored in the sterile container. The sealed container keeps the trocar sterile until it is opened in the medical facility.

Having shown and described various embodiments and examples of the present invention, further adaptations of the methods and apparatuses described herein can be accomplished by appropriate modifications by one of ordinary skill in the art without departing from the scope of the present invention. Several of such potential modifications have been mentioned, and others will be apparent to those skilled in the art. For instance, the specific dimensioned described above will be understood to be nonlimiting examples. Accordingly, the scope of the present invention should be considered in terms of the following claims and is understood not to be limited to the details of structure, materials, or acts shown and described in the specification and drawings.

What is claimed is:

1. A seal for endoscopic instruments, comprising an elastomeric membrane having an opening adapted to receive a surgical instrument, said membrane being configured with a plurality of pleats circumscribing the opening and extending laterally away from the opening, each of said plurality of pleats comprising a plurality of pleat walls defining a height between a peak and an adjacent valley, wherein each of the plurality of pleat walls increase in height as the plurality of pleats extend laterally away from the opening.

2. The seal of claim 1, wherein the pleats are conically arranged.

3. The seal of claim 1, further comprising a wall section circumscribing and connected to the pleats.

4. The seal of claim 3, wherein the wall section is cylindrical.

5. The seal of claim 3, further comprising a radial flange extending laterally from the wall section.

6. The seal of claim 3, further comprising bellows circumscribing and connected to the wall section.

7. The seal of claim 1, further complising a lip defining the opening.

8. The seal of claim 1, comprising only eight pleats.

9. A trocar comprising the seal of claim 1.

10. A method for processing a trocar for surgery, comprising:
   a) obtaining the trocar of claim 9;
   b) sterilizing the trocar; and
   c) storing the trocar in a sterile container.

11. A trocar seal comprising: a) a lip defining and an opening, said lip being adapted to sealingly engage an endoscopic surgical instrument; and b) a plurality of conically arranged linear pleats circumscribing the lip and extending radially away from lip, said plurality of conically arranged linear pleats comprising a plurality of medical tapering walls defining a height between a peak and a valley, wherein each of the plurality of medical tapering walls increase in height as the plurality of conically arranged linear pleats extend radially away from the lip.

12. A trocar comprising the seal of claim 11 positioned in a seal housing.

13. A method for processing a trocar for surgery, comprising:
   a) obtaining the trocar of claim 12;
   b) sterilizing the trocar; and
   c) storing the trocar in a sterile container.

14. The trocar seal of claim 11, further comprising a wall section circumscribing the pleats.

15. The trocar seal of claim 14, further comprising bellows circumscribing the wail section.

16. The trocar seal of claim 14, wherein the wall section has a cylindrical portion.

\* \* \* \* \*